United States Patent
Wada et al.

(10) Patent No.: US 9,688,594 B2
(45) Date of Patent: Jun. 27, 2017

(54) METHOD FOR PRODUCING MODIFIED-GRAPHENE-LIKE CARBON MATERIAL, MODIFIED-GRAPHENE-LIKE CARBON MATERIAL, AND RESIN COMPOSITE MATERIAL CONTAINING MODIFIED-GRAPHENE-LIKE CARBON MATERIAL

(71) Applicants: SEKISUI CHEMICAL CO., LTD., Osaka, Osaka (JP); NIIGATA UNIVERSITY, Niigata, Niigata (JP)

(72) Inventors: Takuya Wada, Osaka (JP); Norio Tsubokawa, Niigata (JP)

(73) Assignees: SEKISUI CHEMICAL CO., LTD., Osaka (JP); NIIGATA UNIVERSITY, Niigata (JP)

( * ) Notice: Subject to any disclaimer, the term of this patent is extended or adjusted under 35 U.S.C. 154(b) by 103 days.

(21) Appl. No.: 14/386,955

(22) PCT Filed: May 14, 2013

(86) PCT No.: PCT/JP2013/063344
§ 371 (c)(1),
(2) Date: Sep. 22, 2014

(87) PCT Pub. No.: WO2013/172316
PCT Pub. Date: Nov. 21, 2013

(65) Prior Publication Data
US 2015/0080513 A1 Mar. 19, 2015

(30) Foreign Application Priority Data

May 14, 2012 (JP) ................................. 2012-110402

(51) Int. Cl.
- *C01B 32/23* (2017.01)
- *C07C 29/48* (2006.01)
- *C01B 31/02* (2006.01)
- *C08K 9/02* (2006.01)
- *C07C 31/00* (2006.01)
- *C08K 5/05* (2006.01)
- *C08K 3/24* (2006.01)
- *C08K 3/20* (2006.01)
- *C08K 3/00* (2006.01)
- *C08K 3/04* (2006.01)
- *C01B 31/04* (2006.01)

(52) U.S. Cl.
CPC .............. *C07C 29/48* (2013.01); *C01B 31/02* (2013.01); *C07C 31/00* (2013.01); *C08K 5/05* (2013.01); *C08K 9/02* (2013.01); *C01B 31/043* (2013.01); *C07C 2103/54* (2013.01); *C08K 3/0008* (2013.01); *C08K 3/04* (2013.01); *C08K 3/20* (2013.01); *C08K 3/24* (2013.01)

(58) Field of Classification Search
None
See application file for complete search history.

(56) References Cited

U.S. PATENT DOCUMENTS

| | | | |
|---|---|---|---|
| 2010/0247892 A1* | 9/2010 | Lee | H01B 1/24 428/221 |
| 2010/0301279 A1 | 12/2010 | Nesper et al. | |
| 2011/0143093 A1 | 6/2011 | Kusunoki et al. | |
| 2012/0145070 A1 | 6/2012 | Kusunoki et al. | |
| 2013/0015409 A1 | 1/2013 | Fugetsu | |

FOREIGN PATENT DOCUMENTS

| | | | |
|---|---|---|---|
| CN | 102225759 A | | 10/2011 |
| CN | 102336404 A | * | 2/2012 |
| JP | 2007-169112 A | | 7/2007 |
| JP | 2010-275186 A | | 12/2010 |
| WO | WO 2010/001686 A1 | | 1/2010 |
| WO | WO-2010/023934 A1 | | 3/2010 |
| WO | WO-2011/016889 A2 | | 2/2011 |
| WO | WO-2011/019095 A1 | | 2/2011 |
| WO | WO-2011/074125 A1 | | 6/2011 |

OTHER PUBLICATIONS

Schniepp, H. C. et al. "Functionalized Single Graphene Sheets Derived from Splitting Graphite Oxide". J. Phys. Chem. B 2006, 110(17), 8535-8539.*
International Search Report for the Application No. PCT/JP2013/063344 mailed Jun. 18, 2013.
Written Opinion of the International Searching Authority (PCT/ISA/237) for Application No. PCT/JP2013/063344 mailed Jun. 18, 2013.
Supplementary Partial European Search Report for the Application No. EP 13 79 0270 dated Dec. 1, 2015.
Database WPI, Week 201243, Thomson Scientific, London, GB; AN2012-C40605, XP002750938.
Written Opinion of the International Searching Authority (PCT/ISA/237) for Application No. PCT/JP2013/063344 mailed Jun. 18, 2013 (English Translation mailed Nov. 27, 2014).
Supplementary European Search Report for the Application No. EP 13 79 0270 dated Mar. 9, 2016.
Pellenbarg, Timothy et al., "Detecting and quantifying oxygen functional groups on graphite nanofibers by fluorescence labeling of surface species", Carbon, 2010, vol. 48, No. 15, pp. 4256-4267.
The First Office Action for the Application No. 201380011296.0 from the State Intellectual Property Office of the People's Republic of China dated Aug. 4, 2015.
European Office Action for the Application No. 13 790 270.6 dated Mar. 14, 2017.

* cited by examiner

*Primary Examiner* — Richard A Huhn
(74) *Attorney, Agent, or Firm* — Cheng Law Group, PLLC

(57) ABSTRACT

Providing a modified-graphene-like carbon material into which hydroxyl groups are introduced. By reacting a graphene-like carbon material with hydrogen peroxide, a hydroxyl group is introduced into the graphene-like carbon material.

7 Claims, No Drawings

METHOD FOR PRODUCING MODIFIED-GRAPHENE-LIKE CARBON MATERIAL, MODIFIED-GRAPHENE-LIKE CARBON MATERIAL, AND RESIN COMPOSITE MATERIAL CONTAINING MODIFIED-GRAPHENE-LIKE CARBON MATERIAL

TECHNICAL FIELD

The present invention relates to a method for producing a modified-graphene-like carbon material into which a hydroxyl group is introduced, a modified-graphene-like carbon material, and a resin composite material containing a modified-graphene-like carbon material.

BACKGROUND ART

Graphite is a laminated body formed by laminating exfoliated graphite. By peeling graphite, a graphene-like carbon material such as exfoliated graphite having the number of lamination smaller than graphite, graphene or the like is obtained. Since the graphene-like carbon material excels in conductivity and heat conductivity, application to a conductive material, a heat-conductive material and the like is expected.

Moreover, a resin composite material is also formed by forming a composite of a graphene-like carbon material with a resin or the like. For the purpose of increasing affinity of a graphene-like carbon material for a resin or the like, it is known that the graphene-like carbon material is modified. For example, Patent Literature 1 discloses a denatured carbon material in which a fragment obtained by radical decomposition of an azo radical polymerization initiator containing carboxyl groups is added to a carbon material having a graphene sheet structure.

CITATION LIST

Patent Literature

Patent Literature 1: Japanese Patent Laid-Open No. 2007-169112

SUMMARY OF INVENTION

Technical Problem

Under the circumstances, a novel modified-graphene-like carbon material is required.

It is a main object of the present invention to provide a modified-graphene-like carbon material into which a hydroxyl group is introduced.

Solution to Problem

According to a method for producing a modified-graphene-like carbon material of the present invention, by reacting a graphene-like carbon material with hydrogen peroxide, a hydroxyl group is introduced into the graphene-like carbon material.

In a certain aspect of the method for producing a modified-graphene-like carbon material of the present invention, the introduction of the hydroxyl group into the graphene-like carbon material is performed in the presence of an iron catalyst.

A modified-graphene-like carbon material of the present invention is obtained by the above-described producing method.

In a modified-graphene-like carbon material of the present invention, the amount of the hydroxyl group as measured by a quantitative method using 2,2'-diphenyl-1-picrylhydrazyl is 0.3 mmol/g to 10.0 mmol/g.

In a certain aspect of the modified-graphene-like carbon material of the present invention, the amount of a carboxyl group as measured by a quantitative method using $NaHCO_3$ is 1.0 mmol/g or less.

A resin composite material of the present invention is obtained by dispersing the modified-graphene-like carbon material of the present invention in a resin.

Advantageous Effects of Invention

According to the present invention, a modified-graphene-like carbon material into which a hydroxyl group is introduced can be provided.

DESCRIPTION OF EMBODIMENTS

Hereinafter, a method for producing a modified-graphene-like carbon material, a modified-graphene-like carbon material, and a resin composite material containing a modified-graphene-like carbon material, according to the present invention will be described in detail.

Method for Producing Graphene-Like Carbon Material

In a method for producing a graphene-like carbon material according to the present invention, by reacting a graphene-like carbon material with hydrogen peroxide, a hydroxyl group is introduced into the graphene-like carbon material. A modified-graphene-like carbon material of the present invention is one obtained by introducing a hydroxyl group into the graphene-like carbon material as a raw material.

The graphene-like carbon material means graphene or exfoliated graphite. In the present invention, the exfoliated graphite is a laminated body of a graphene sheet composed of one-layer graphene. The exfoliated graphite is a laminated body of a graphene sheet, which is thinner than original graphite. The number of lamination of the graphene sheet in the exfoliated graphite is 2 or more, and generally 200 or less. The exfoliated graphite is commercially available or can be produced by a conventionally-known method. The exfoliated graphite can be obtained by, for example, peeling treatment of graphite. The exfoliated graphite can be obtained by, for example, a chemical treatment method of performing heat treatment after inserting ions such as nitrate ions between layers of graphite, a physical treatment method of applying ultrasonic waves to graphite, an electrochemical method of performing electrolysis using graphite as a working electrode.

The graphene-like carbon material has a shape having a large aspect ratio. Thus, when the modified-graphene-like carbon material is uniformly dispersed in a resin composite material described below, a reinforcing effect with respect to external force applied in a direction intersecting a lamination surface of the graphene-like carbon material can be effectively increased. It is to be noted that, if the aspect ratio of the modified-graphene-like carbon material is too small, the reinforcing effect with respect to the external force applied in the direction intersecting the lamination surface may not be sufficient. If the aspect ratio of the modified-graphene-like carbon material is too large, the effect is saturated and a further reinforcing effect may not be expected. Thus, the aspect ratio of the graphene-like carbon material is preferably 50 or more, and more preferably 100 or more. Furthermore, the aspect ratio of the graphene-like carbon material is preferably 5000 or less. It is to be noted that the aspect ratio of the graphene-like carbon material in the present invention means a ratio of a maximum dimension of the graphene-like carbon material in the lamination surface direction to the thickness of the graphene-like carbon material.

In order to increase the mechanical strength of the resin composite material, the average particle diameter of the graphene-like carbon material is preferably about 1 µm to 5 µm, and more preferably about 3 µm to 5 µm.

The reaction of the graphene-like carbon material with hydrogen peroxide can be performed by, for example, mixing the graphene-like carbon material and hydrogen peroxide water. The concentration of hydrogen peroxide in the hydrogen peroxide water may be about 10 mass % to 27 mass %. In addition, the reaction temperature may be about 0° C. to 50° C. The reaction time may be 0.5 hours to 48 hours. The reaction of the graphene-like carbon material with hydrogen peroxide may be performed under the atmosphere or in the presence of inert gas such as argon and nitrogen.

The reaction of the graphene-like carbon material with hydrogen peroxide is preferably performed in the presence of an iron catalyst. Accordingly, introduction of the hydroxyl group into the graphene-like carbon material can be effectively performed. Examples of a method of performing the reaction of the graphene-like carbon material with hydrogen peroxide in the presence of the iron catalyst include a method of using a Fenton's reagent. It is to be noted that the Fenton's reagent is a solution of hydrogen peroxide and an iron catalyst (divalent iron ion). The reaction of the graphene-like carbon material with hydrogen peroxide is preferably performed by using the Fenton's reagent. Accordingly, introduction of the hydroxyl group into the graphene-like carbon material can be effectively performed.

As described above, by reacting the graphene-like carbon material with hydrogen peroxide, the modified-graphene-like carbon material obtained by introducing the hydroxyl group into the graphene-like carbon material can be obtained.

Modified-Graphene-Like Carbon Material

The modified-graphene-like carbon material according to the present invention can be produced by, for example, the above-described method for producing a modified-graphene-like carbon material according to the present invention.

The modified-graphene-like carbon material according to the present invention is one obtained by introducing the hydroxyl group into the graphene-like carbon material. In the modified-graphene-like carbon material, the amount of the hydroxyl group as measured by a quantitative method using 2,2'-diphenyl-1-picrylhydrazyl is 0.3 mmol/g to 10.0 mmol/g. In order to increase affinity of the modified-graphene-like carbon material for a polar solvent, the amount of the hydroxyl group when measuring the modified-graphene-like carbon material by the quantitative method using 2,2'-diphenyl-1-picrylhydrazyl is preferably about 0.3 mmol/g to 5.0 mmol/g, and more preferably about 0.35 mmol/g to 3.0 mmol/g.

In the modified-graphene-like carbon material, the amount of the carboxyl group as measured by a quantitative method using $NaHCO_3$ is preferably 1.0 mmol/g or less.

The aspect ratio of the modified-graphene-like carbon material is the same as the above-described aspect ratio of the graphene-like carbon material. The average particle diameter of the modified-graphene-like carbon material is the same as the above-described average particle diameter of the graphene-like carbon material. The number of lamination of the graphene sheet of the modified-graphene-like carbon material is the same as the above-described number of lamination of the graphene sheet of the exfoliated graphite.

Resin Composite Material

The resin composite material of the present invention is obtained by dispersing the modified-graphene-like carbon material of the present invention in a resin.

With respect to 100 parts by mass of the resin, the resin composite material preferably contains about 0.01 parts by mass to about 40 parts by mass, and more preferably contains about 0.1 parts by mass to about 20 parts by mass of the modified-graphene-like carbon material. Accordingly, the mechanical strength of the resin composite material can be effectively increased.

Examples of the resin include a thermoplastic resin and a thermosetting resin. As the resin, a thermoplastic resin is preferable.

As the thermoplastic resin, a known thermoplastic resin can be used without being particularly limited. Specific examples of the thermoplastic resin include polyolefin, polystyrene, polyacrylate, polyacrylonitrile, polyester, polyamide, polyurethane, polyethersulfone, polyetherketone, polyimide, polydimethylsiloxane, and a copolymer of at least two kinds thereof. The thermoplastic resin contained in the resin composite material may be one kind or two kinds or more.

As the thermoplastic resin, polyolefin is preferable. Polyolefin is inexpensive, and is easily molded by heating. Thus, by using polyolefin as the thermoplastic resin, production cost of the resin composite material can be reduced, and the resin composite material can be easily molded.

Examples of the polyolefin include polyethylene, polypropylene, polyethylene resins such as an ethylene homopolymer, an ethylene-α-olefin copolymer, an ethylene-(meth)acrylic acid copolymer, an ethylene-(meth)acrylic acid ester copolymer, and an ethylene-vinyl acetate copolymer, polypropylene resins such as a propylene homopolymer, a propylene-α-olefin copolymer, a propylene-ethylene random copolymer, and a propylene-ethylene block copolymer, a butene homopolymer, and a homopolymer or a copolymer of conjugated dienes such as butadiene and isoprene. As the thermoplastic resin, polypropylene resins are particularly preferable.

Conventionally, it was extremely difficult to selectively introduce a large number of hydroxyl groups into a graphene-like carbon material. For example, there is a method of introducing the hydroxyl group by a process such as mixed acid (mixed liquid of nitric acid and sulfuric acid) treatment, but there is a problem in that, by such a method, a large number of carboxyl groups are also introduced together with the hydroxyl group.

In contrast, according to the producing method of the present invention, for example, the modified-graphene-like carbon material having the amount of the hydroxyl groups as measured by the quantitative method using 2,2'-diphenyl-1-picrylhydrazyl of 0.3 mmol/g to 10.0 mmol/g can be easily produced. Since a large number of hydroxyl groups are introduced, such a modified-graphene-like carbon material has high affinity for a polar solvent, and can be uniformly dispersed in the polar solvent. Moreover, by using the hydroxyl group in the modified-graphene-like carbon material, a urethane bond can be formed with a compound having an isocyanate group.

Hereinafter, the present invention will be clarified by specifically offering Example and Comparative Example. It is to be noted that the present invention is not limited to the following Example.

Production of Exfoliated Graphite

As a raw material graphite sheet, Item Number: PF100-UHP manufactured by Toyo Tanso Co., Ltd was prepared. According to the same producing method as the graphite sheet, by lowering a rolling ratio in rolling treatment, a low-density graphite sheet having a density of 0.7 and a thickness of 1 mm was prepared.

The graphite sheet having a density of 0.7 obtained as described above was cut into a size of 5 cm×5 cm to obtain a graphite sheet as an electrode material. Two slits were formed in the graphite sheet by being cut with a cutter knife such that the length of the slits was 1 cm. An electrode made of Pt was inserted into the graphite sheet in which the above-described two slits were formed. The graphite sheet prepared in this manner and used as a working electrode (anode) was immersed in a nitric acid aqueous solution having a concentration of 60 wt %, together with a counter electrode (cathode) made of Pt and a reference electrode made of Ag/AgCl. Regarding the immersion, the graphite sheet part between the lower end and the height of 4 cm of the 5 cm×5 cm graphite sheet was immersed in the nitric acid aqueous solution, and the upper part of the graphite sheet was not immersed in the nitric acid aqueous solution. Electrochemical treatment was performed by application of a direct voltage. In this manner, a part of the original graphite sheet used as a working electrode, which was immersed in the nitric acid aqueous solution, was obtained as expanded graphite.

Next, the obtained expanded graphite was dried at low temperature and cut into 1 cm squares, one of them was put in a carbon crucible, and electromagnetic induction heating treatment was performed. As an induction heating apparatus, MU1700D manufactured by SK Medical Electronics Co., Ltd. was used, and the treatment was performed with the amount of current of 14 A under an argon gas atmosphere such that the highest achieving temperature was 550° C. When the expanded graphite was exfoliated by electromagnetic induction heating, and a specific surface area of powder of the obtained exfoliated graphite was measured using nitrogen gas with a specific surface area measurement apparatus ASAP-2000 manufactured by Shimadzu Corporation, a specific surface area of 640 m$^2$/g was indicated by one measurement.

The exfoliated graphite obtained as described above was used in the following Example 1 and Comparative Example 1.

Example 1

In the atmosphere, 0.5 g of the exfoliated graphite obtained as described above, 2.8 ml of concentrated sulfuric acid, and 150 ml of pure water were put in a four-neck flask to which a nitrogen gas introducing tube, a thermometer, and two dropping funnels were attached, and the inside of the flask was substituted with nitrogen gas. Hydrogen peroxide water (27%) was put in one dropping funnel, and 27.8 g of $FeSO_4/7H_2O$, 5.6 ml of concentrated sulfuric acid, and 57 ml of pure water were put in the other dropping funnel. When the hydrogen peroxide water and the $FeSO_4$ solution were dropped from the two dropping funnels while cooling the four-neck flask with an ice-water bath, the temperature of the reaction liquid was rapidly increased, and thus, the dropping was performed for about 30 minutes while adjusting the dropping rate such that the temperature of the reaction liquid did not exceed 20° C. After that, the reaction was performed for 48 hours with the reaction liquid maintained at 20° C. After the reaction, the reaction liquid was neutralized with sodium hydroxide and filtered to obtain a modified-graphene-like carbon material into which hydroxyl groups were introduced. In the modified-graphene-like carbon material into which hydroxyl groups were introduced, the amount of the hydroxyl groups as measured by a quantitative method using 2,2'-diphenyl-1-picrylhydrazyl was 0.39 mmol/g. In addition, when measuring the amount of carboxyl groups by a quantitative method of carboxyl groups using $NaHCO_3$, the carboxyl groups was negligibly small in amount.

Comparative Example 1

A stirrer bar, 0.2 g of the exfoliated graphite obtained as described above, and 50 ml of mixed acid ($HNO_3/H_2SO_4=\frac{1}{3}$ (v/v)) were put in a 100 ml eggplant flask to which a reflux condenser was attached, and the reaction was performed at 40° C. for 10 hours while being stirred with a magnetic stirrer. After the reaction, the reaction product was added to a large amount of pure water and filtered, and was washed until the filtrate became neutral to obtain a modified-graphene-like carbon material into which hydroxyl groups were introduced. The amount of the hydroxyl groups introduced of the modified-graphene-like carbon material into which hydroxyl groups were introduced as measured by a quantitative method using 2,2'-diphenyl-1-picrylhydrazyl was 0.28 mmol/g. When measuring the amount of carboxyl groups by a quantitative method of carboxyl groups using $NaHCO_3$, the amount of carboxyl groups was 1.52 mmol/g.

The invention claimed is:

1. A modified-graphene-like carbon material, wherein an amount of a hydroxyl group as measured by a quantitative method using 2,2'-diphenyl-1-picrylhydrazyl is 0.3 mmol/g to 10.0 mmol/g, and
    wherein an amount of a carboxyl group as measured by a quantitative method using $NaHCO_3$ is 1.0 mmol/g or less.

2. A resin composite material obtained by dispersing the modified-graphene-like carbon material according to claim 1 in a resin.

3. A modified-graphene-like carbon material obtained by a method comprising reacting a graphene-like carbon material with hydrogen peroxide to introduce a hydroxyl group into the graphene-like carbon material,
    wherein an amount of the hydroxyl group in the modified-graphene-like carbon material as measured by a quantitative method using 2,2'-diphenyl-1-picrylhydrazyl is 0.3 mmol/g to 10.0 mmol/g, and
    wherein an amount of a carboxyl group as measured by a quantitative method using $NaHCO_3$ is 1.0 mmol/g or less.

4. A resin composite material obtained by dispersing the modified-graphene-like carbon material according to claim 3 in a resin.

5. A modified-graphene-like carbon material obtained by a method comprising reacting a graphene-like carbon material with hydrogen peroxide to introduce a hydroxyl group into the graphene-like carbon material, wherein the introduction of the hydroxyl group into the graphene-like carbon material is performed in the presence of an iron catalyst, wherein an amount of the hydroxyl group in the modified-graphene-like carbon material as measured by a quantitative method using 2,2'-diphenyl-1-picrylhydrazyl is 0.3 mmol/g to 10.0 mmol/g, and wherein an amount of a carboxyl group as measured by a quantitative method using $NaHCO_3$ is 1.0 mmol/g or less.

6. A method for producing the modified-graphene-like carbon material according to claim 3, comprising reacting a graphene-like carbon material with hydrogen peroxide to introduce a hydroxyl group into the graphene-like carbon material.

7. The method for producing the modified-graphene-like carbon material according to claim 6, wherein the introduction of the hydroxyl group into the graphene-like carbon material is performed in the presence of an iron catalyst.

* * * * *